United States Patent [19]

Garland et al.

[11] Patent Number: 4,992,563

[45] Date of Patent: Feb. 12, 1991

[54] BENZOPYRAN INTERMEDIATES FOR USE IN MANUFACTURING THROMBOXANE $A_2$ ANTAGONISTS

[75] Inventors: Robert B. Garland; Masateru Miyano, both of Northbrook, Ill.

[73] Assignee: National Research Development Corporation, London, England

[21] Appl. No.: 283,671

[22] Filed: Dec. 13, 1988

[51] Int. Cl.[5] .................. C07D 311/78; C07D 413/02; C07C 59/48; C07C 211/01

[52] U.S. Cl. ...................... 549/386; 549/281; 546/269; 548/159; 548/217; 548/221; 562/427; 562/470; 564/82; 564/88; 564/308; 568/326; 568/328; 568/376

[58] Field of Search ............... 549/281, 386; 546/269; 548/159, 217, 221

[56] References Cited

U.S. PATENT DOCUMENTS 4,416,896 11/1983 Nakane et al. ................ 549/281
4,456,617 6/1984 Nakane et al. ................ 549/281

OTHER PUBLICATIONS

Wilson, et al "Prostaglandin Endoperoxide . . . " Advances in Pros., Throm. & Leukotriene Research vol. 14, 1985, pp. 393–425.

Nakane et al "Aza–Substituted . . . " Advances in Pros., Throm. & Leukotriene Research, 1985, vol. 15, 291.

Sprague et al "Stereocontrolled Synthesis of . . . " Advances in Pros., Throm. & Leukotriene Research, 1980, vol. 6, pp. 493–496.

Christl et al. Chem. Abstracts; vol. 103, No. 23; 195960p (1985).

Furuichi et al. Chem. Abstracts, vol. 82, No. 17; 111970d (1975).

Greico et al., Chem. Abstracts, vol. 80, No. 17, 95178c (1974).

Armstrong, R. A. "Competitive Antagonism at Thromboxane Receptors in Human Platelets" Br. J. Pharmac. (1985) 84, pp. 595–607.

*Primary Examiner*—Mary C. Lee
*Assistant Examiner*—J. Richter
*Attorney, Agent, or Firm*—Nixon & Vanderhye

[57] ABSTRACT

This invention relates to several intermediates useful in preparing thromboxane $A_2$ inhibiting (±)7-[3α-[1-[[(phenylamino)-thioxomethyl]hydrazono]ethyl]-1α, 4α-bicyclo[2.2.1]hept-2β-yl]-heptenoic acids and useful derivatives thereof from (±)octahydro-1α-methyl-3aα, 7aα-4α,7α-methano-2H-inden-2-ones.

3 Claims, No Drawings

BENZOPYRAN INTERMEDIATES FOR USE IN MANUFACTURING THROMBOXANE A₂ ANTAGONISTS

BACKGROUND OF THE INVENTION

1. Field of the Invention

This invention relates to a novel process that permits the unexpectedly efficient and convenient preparation of thromboxane $A_2$ inhibiting $(\pm)$-7-[3α-[1-[[(phenylamino)thioxomethyl]hydrazono]ethyl]-1α,4α-bicyclo[2.2.1]hept-2β-yl]heptenoic acids (hereinafter called "bicycloheptenoic acids") of Example 2 of U.S. Pat. No. 4,596,823, as well as its geometric isomer. The process is easily and conveniently adapted to the synthesis of a great number of derivatives of the subject bicycloheptenoic acids as disclosed in U.S. Pat. No. 4,596,823, having the general formula

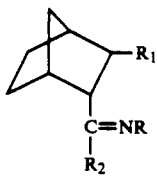

from compounds of the general formula

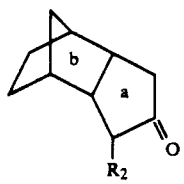

in which $R_1$ is a group of the formula $R'-COQ$ where $R'$ is selected from the group consisting of
—(CH₂)ⱼ—
where j is an integer from 4 to 8; and —CH₂—CH=CH—(CH₂)ₘ—
where m is an integer from 1 to 5; and COQ is carboxy, a physiologically acceptable carboxylate salt (including such specific examples as alkali metals such as sodium, quaternary ammonium ions, or amines such as tris, i.e. 2-amino-2-hydroxymethylpropane 1,3-diol), a $C_1$-$C_5$ alkyl ester or $CONHSO_2CH_3$;

$R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, napthyl, fluorenyl, dibenzocyclohexyl, dibenzocycloheptyl, pyridyl, benzthiazolyl, dihydrobenzthiazolyl, N-methyldihydroοenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups; and R is a group —$OR_3$, —$OR_4$, —A—$R_3$ or —N=$R_5$ in which A is —NH—, —NHCO— and —NHCONH—, —NH CO CH₂N(R₆)—, —NH SO₂—, or —NH CS NH— and wherein $R_3$ is a $C_{1-10}$ aliphatic hydrocarbon group, a group Ar or a $C_{1-10}$ aliphatic hydrocarbon group substituted by one or more groups selected from Ar, OAr and SAr; $R_4$ is substituted through an oxygen atom by a $C_{1-10}$ aliphatic hydrocarbon group which is itself substituted by one or more groups Ar; $R_5$ is a $C_{1-10}$ alphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyldihydrobenzoxazolylidene group or such a group substituted on a benzene ring or rings thereof by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups, or a $C_{1-10}$ aliphatic hydrocarbon group substituted by one or more groups selected from Ar, OAr and SAr; and $R_6$ is hydrogen, a $C_{1-10}$ aliphatic hydrocarbon group, a group Ar or a $C_{1-10}$ aliphatic hydrocarbon group substituted by one or more groups selected from Ar, OAr and SAr. These derivatives are more fully described in U.S. Pat. No. 4,596,823, the disclosure of which is incorporated herein by reference.

More specifically, this invention relates to a process for preparing bicycloheptenoic acids of Formula I in improved overall yield and purity by reacting a cyclic hemiacetal with a phosphonium ylide derived from an omega substituted fatty acid, oxidizing the resultant product to the corresponding ketone, and forming a hydrazone from the corresponding ketone.

This invention also relates to novel intermediates employed in the preparation of the thromboxane $A_2$ inhibiting bicycloheptenoic acid derivatives of Formula I.

SUMMARY OF THE INVENTION

This invention relates to a process for preparing compounds of the general formula

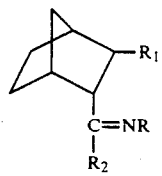

I wherein R, $R_1$ and $R_2$ are as previously described, which comprises the steps of:

(a) reacting a compound of the general formula

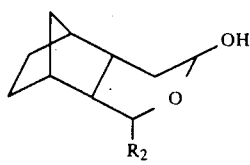

II wherein $R_2$ is as defined above, in the presence of a base with a compound of the general formula

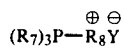

III wherein $R_8$ is as defined above for $R_1$, with the proviso that $R_8$ has two fewer methylene groups than the species chosen for $R_1$, $R_7$ is aryl and Y is halogen, to yield a compound of the general formula

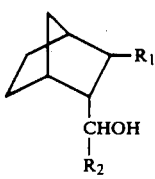

wherein $R_1$ and $R_2$ are as defined above;

(b) oxidizing the product of (a) to yield a compound of the general formula

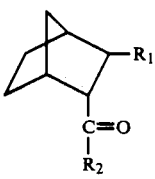

wherein $R_1$ and $R_2$ are as defined above; and (c) reacting the product of (b) with an amine of the formula

wherein R is as defined above. Additionally, prior to reacting the product of (b) with the above-described amine, the product of (b) can be inverted at the chiral center adjacent to the carbonyl group to yield its trans isomer.

More specifically, the process of the invention proceeds by (a) preparing a compound of the general formula:

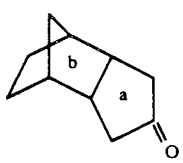

(b) modifying the compound of (a) to yield a compound of the formula

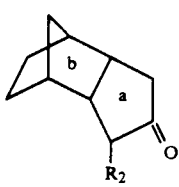

wherein $R_2$ is as defined above;

(c) oxidizing, by peracid oxidation, the ring 'a' of the product of (b) to yield a compound of the general formula

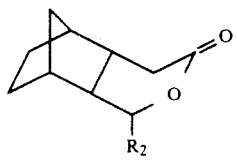

wherein $R_2$ is as defined above;

(d) reducing the product of (c) to yield a compound of the general formula

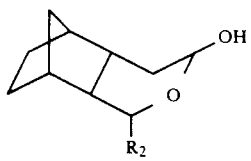

wherein $R_2$ is defined above;

(e) reacting the product of (d) in the presence of a base with a compound of the formula:

$$(R_7)_3 \overset{\oplus}{P} - \overset{\ominus}{R_8} Y \qquad \text{III}$$

wherein $R_8$ is as defined above for $R_1$ with the proviso that $R_8$ has two fewer methylene groups than the species chosen for $R_1$, $R_7$ is aryl, and Y is halogen, to yield a compound of the general formula

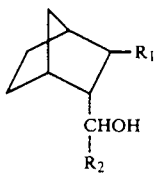

wherein $R_1$ and $R_2$ are as defined above;

(f) oxidation of the product of (e) to yield a compound of the general formula

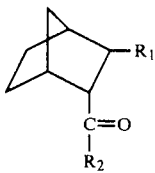

wherein $R_1$ and $R_2$ are as defined above; and (g) hydrazone formation of the product of (f) with an amine of the general formula:

wherein R is as defined above.

Likewise, the product of (f) can be inverted at the chiral center adjacent to the carbonyl group to yield its trans isomer prior to hydrazone formation.

This invention also relates to intermediate compounds of the general formula

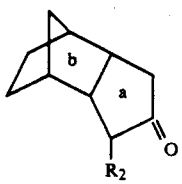

VII and the pharmaceutically acceptable salts thereof, wherein $R_2$ is as defined above.

This invention further relates to intermediate compounds of the general formula

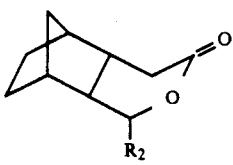

VIII and the pharmaceutically acceptable salts thereof, wherein $R_2$ is as defined above.

This invention still further relates to intermediate compounds of the general formula

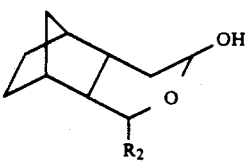

II and the pharmaceutically acceptable salts thereof, wherein $R_2$ is as defined above.

This invention yet further relates to intermediate compounds of the general formula

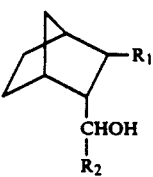

IV and the pharmaceutically acceptable salts thereof, wherein $R_1$ and $R_2$ are as defined above.

DETAILED DESCRIPTION OF THE INVENTION

Thromboxane $A_2$($TXA_2$), which is derived from arachidonic acid via prostaglandin $H_2$($PGH_2$), is implicated in several potentially noxious actions on various body systems, including platelet aggregation, bronchoconstriction and pulmonary and systemic vasoconstriction. Thus $TXA_2$ may be involved in the Normal sealing of blood vessels following injury, but in addition may contribute to pathological intravascular clotting or thrombosis. Furthermore, the constrictor actions of $TXA_2$ on bronchiolar, pulmonary vascular and systemic vascular smooth muscle may be important in the development of several anaphyllactic conditions including bronchial asthma. Furthermore, evidence exists that implicates $TXA_2$ as well as $PGH_2$ in the pathogenesis of inflammation.

It is an object of the present invention to provide a route of synthesis resulting in greater convenience, efficiency and yield of compounds having activity at thromboxane $A_2$ receptor sites, and most especially of those compounds having such activity which are inhibitors of thromboxane $A_2$ activity and are therefore of interest in one or more areas of medical treatment including the treatment of thrombotic disorders, the treatment of anaphylactic disease states, and treatments utilizing anti-inflammatory agents.

This invention prepares compounds, by the following general method of Scheme A, from (±)octahydro-1α-methyl-3aα, 7aα-4α,7α-methano-2H-inden-2-one (formula III), or derivatives thereof, which can be prepared by methods well known to those skilled in the art.

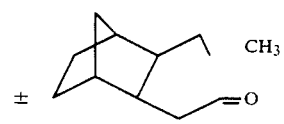

Scheme A

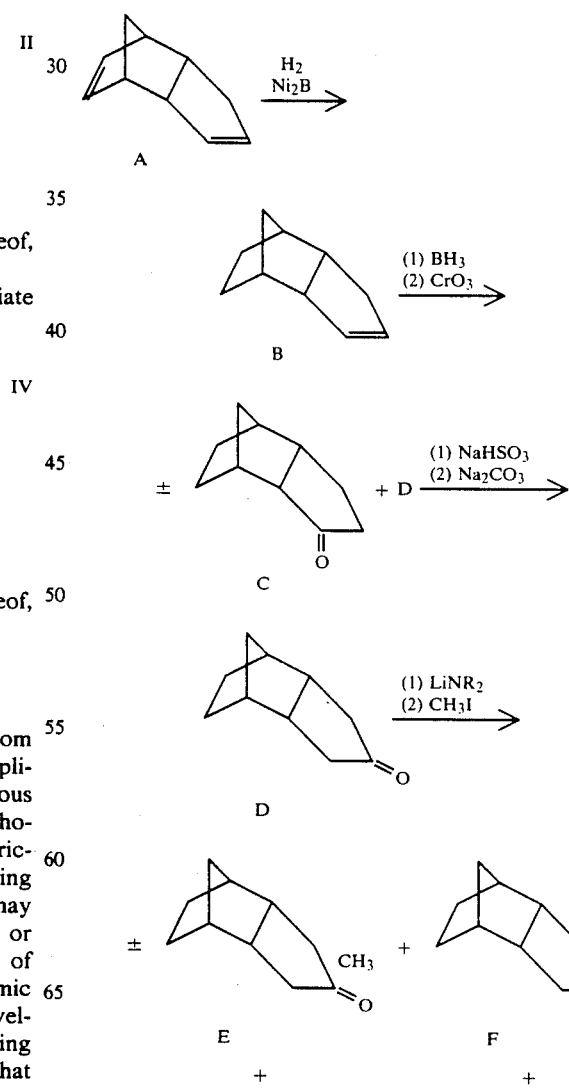

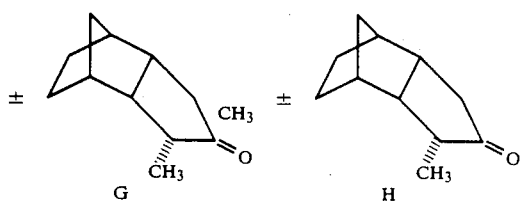
Following the preparation of compound E by such well-known methods, the synthesis of the desired compounds preferably proceeds, for example, as follows in Scheme B:
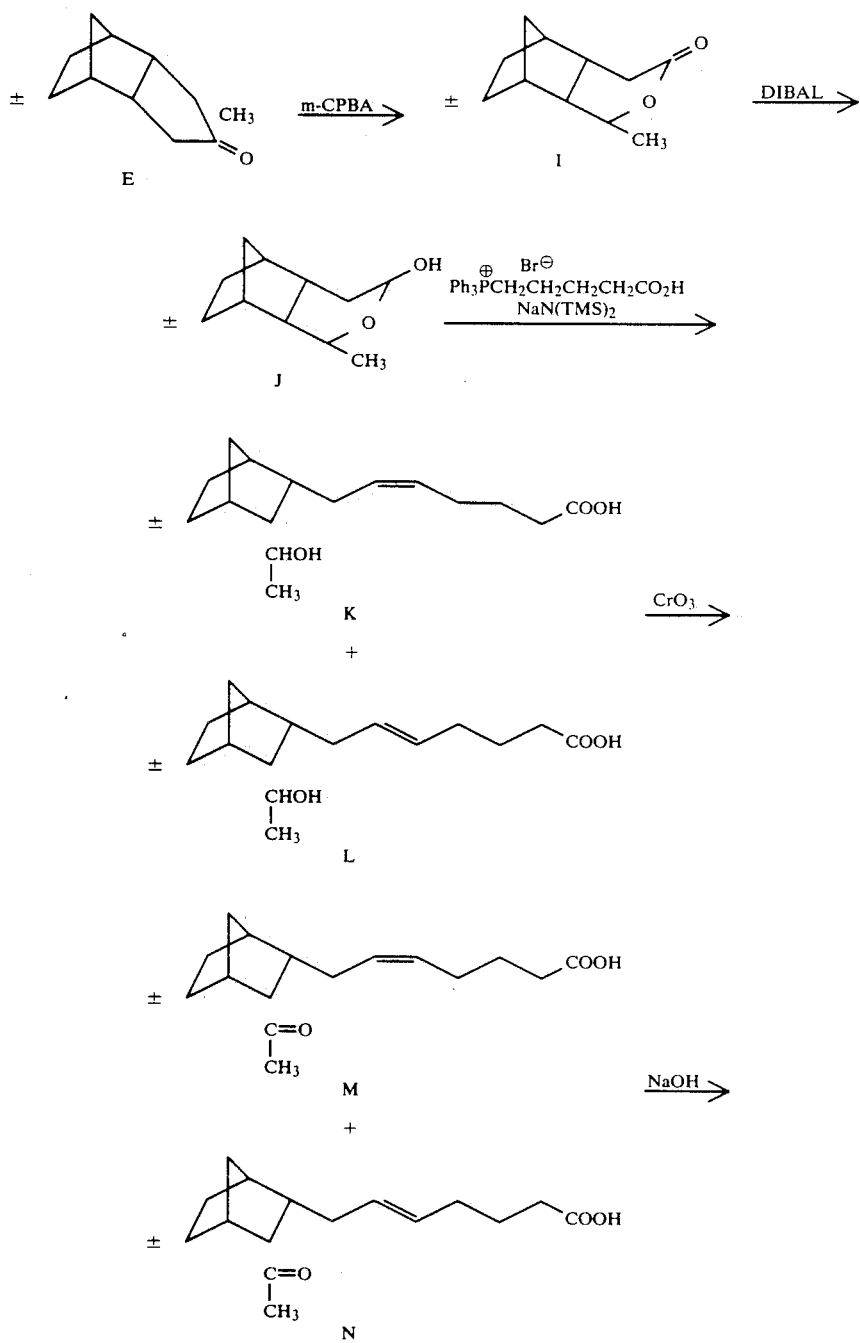

-continued

Scheme B

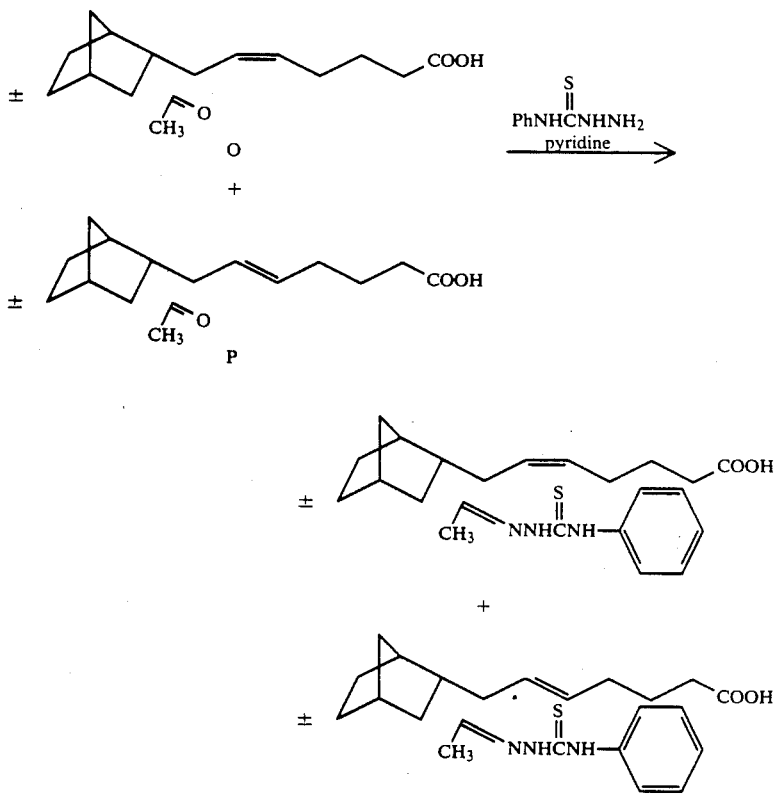

Where the group R' is of the form —(CH$_2$)$_j$—, it will be necessary to include a reduction step in order to convert the initially formed group R' having the formula —CH$_2$—CH=CH—(CH$_2$)$_m$—, where m is an integer equal to j-3, to the desired group —(CH$_2$)$_j$—. This is done by reduction either of the intermediate of formula IV or, more preferably, the intermediate of formula V, by reaction with hydrogen in the presence of a suitable catalyst, such as palladium on charcoal.

The preferred embodiments of this invention include intermediate compounds of the following general structure, used in the preparation of the corresponding thromboxane A$_2$ inhibiting bicycloheptenoic acid derivatives:

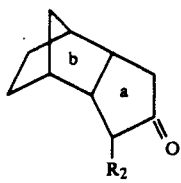

and the pharmaceutically acceptable salts thereof, wherein R$_2$ is as defined above.

More specifically, the preferred embodiments include compounds of the above formula wherein R$_2$ is C$_{1-10}$ aliphatic hydrocarbon, and most especially preferred is the above compound wherein R$_2$ is methyl, namely (±)octahydro-1α-methyl -3aα,7aα-4α,7α-methano-2H-inden-2-one,

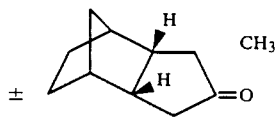

Secondarily illustrative of the preferred embodiments of this invention include compounds of the following general structure, likewise used in the preparation of corresponding thromboxane A$_2$ inhibiting bicycloheptenoic acid derivatives:

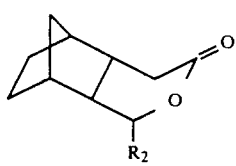

and the pharmaceutically acceptable salts thereof, wherein R$_2$ is as defined above.

More specifically, the preferred embodiments include compounds of the above formula wherein R$_2$ is C$_{1-10}$ aliphatic hydrocarbon, and most especially preferred is the above compound wherein R$_2$ is methyl, namely (±)octahydro-1α-methyl -4aα,8aα,-5α,8α-methano-3H-2-benzopyran-3-one,

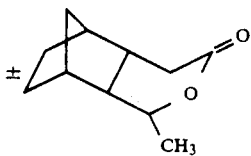

Thirdly illustrative of preferred embodiments of this invention include compounds of the following general structure, likewise used in the preparation of corresponding thromboxane A₂ inhibiting bicycloheptenoic acid derivatives.

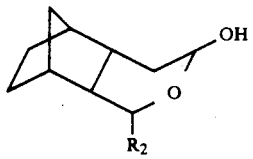

and the pharmaceutically acceptable salts thereof, wherein $R_2$ is as defined above.

More specifically, the preferred embodiments include compounds of the above formula wherein $R_2$ is $C_{1-10}$ aliphatic hydrocarbon, and most especially preferred is the above compound wherein $R_2$ is methyl, namely (±)octahydro 1α-methyl-4aα,8aα,-5α,8α-methano-1H-2-benzopyran-3-ol,

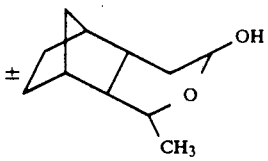

Fourthly illustrative of preferred embodiments of this invention include compounds of the following general structure, used in the preparation of corresponding thromboxane A₂ inhibiting bicycloheptenoic acid derivatives

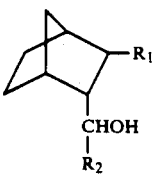

and the pharmaceutically acceptable salts thereof, wherein $R_1$ and $R_2$ are as defined above.

More specifically, the preferred embodiments include compounds of the above formula wherein $R_1$ is a group of the formula R'-COQ where R' is —(CH₂)ⱼ— where j is an independent integer of from 5 to 7, especially 6, or particularly where R' is —CH₂—CH=CH—(CH₂)ₘ where m is an independent integer of from 1 to 5, especially 2 to 4, and particularly 3; $R_2$ is $C_{1-10}$ aliphatic hydrocarbon, particularly methyl; and COQ is carboxy. Other preferred embodiments are the above compound wherein COQ is carboxy, m is 3 and $R_2$ is methyl, namely (±)7-[3β-(1R*-hydroxyethyl)-1α,4α-bicyclo[2.2.1]hept-2β-yl]-5Z-heptenoic acid,

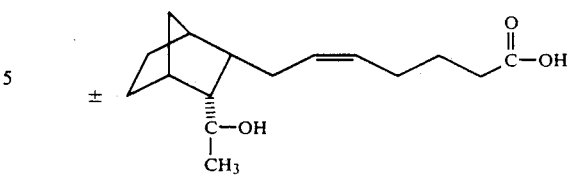

The following examples further illustrate details for the method of preparation of the invention and for compounds of the invention. The invention, which is set forth in the foregoing disclosure, is not to be construed or limited in spirit or in scope by these examples. Those skilled in the art will readily understand that known variations of the conditions of the following preparative procedures can be used to prepare these compounds. All temperatures are degrees Celsius unless otherwise noted. In these reactions, it is also possible to make use of variations which are in themselves known, but are not mentioned here in greater detail. The compounds of the invention are readily prepared according to one of the following reaction schemes, or modifications thereof, using readily available starting materials, reagents and conventional synthesis procedures.

EXAMPLE 1

(±)3aα,4,7,7aα-tetrahydro-4α,7α-methano-1H-indene, A. Commercial dimer is suitable for use, if it has been protected from the air. A sample of a freshly opened Aldrich (Aldrich Chemical Company, 940 West St. Paul Ave., Milwaukee, Wis.) bottle showed only traces of impurities not present in a sample prepared by cracking the dimer and letting it dimerize over a period of weeks and then distilling under reduced pressure. The dimer is, however, susceptible to air oxidation. Old bottles have solids present and upon cracking provide quantities of water and leave a large pot residue.

EXAMPLE 2

(±)3aα,4,5,6,7,7aα-hexahydro-4α,7α-methano-1H-indene, B. The hydrogenation over Nickel Boride, as described by Brown et al (Brown, H. C.; Rothberg, I.; VanderJagt, D. L., *J. Org. Chem.* 1972, 37, 4098–4100) works quite well. Other catalysts tried gave extensive overreduction.

EXAMPLE 3

(±)octhydro-3aα,7aα-4α,7α-methano-2H-inden-2-one, D. The hydroboration should be carried out in the manner described by Brown, ibid.

The bisulfite adduct is thick and hard to filter but it must be washed well with ether to remove all of the unsymmetrical ketone, (±)octahydro-3aα,7aα,-4α,7α-methano-1H-inden-1-one, C.

EXAMPLE 4

(±)octahydro-1α-methyl-3aα,7aα-4α,7α-methano-2H-inden-2-one, E. To a solution of 6.9 mL (5.93 g, 41.9 mmole) of N-isopropylcyclohexylamine in 20 mL of dry THF cooled in a −78° bath was added 25 mL of 1.58 M n-butyllithium in hexane. After 15 min a solution of 5.62 g (37.5 mmole) of D in 20 mL of THF was added over 20 min. After 15 min more, 5 mL (11.4 g, 80 mmole) of methyl iodide was added quickly. (Alternatively, a methyl sulfonate can be used, such as methyl benzenesulfonate, methyl toluenesulfonate or methyl methanesulfonate.) After 30 min more, the mixture was allowed to warm to room temperature. After the addition of water (50 mL) the mixture was extracted twice with ether. After washing with water and brine and then drying over sodium sulfate, the solvents were evaporated and the residue was chromatographed (Flash, hexane-EtOAc 99:1) to provide first 596 mq (9%) of (±)octahydro-1α,3α-dimethyl-3aα,7aα-4α,7α-methano-2H-inden-2-one, F, followed by 3.81 g (62%) of E, and then a small amount of crude D. In some runs the early part of the E fraction contained (±)octahydro-1,1-dimethyl -3aα,7aα-4α,7α-methano-2H-inden-2-one, G. In a run which was allowed to stand at room temperature overnight before workup, a small amount of the isomeric (±)octahydro -1α-methyl-3aαβ,7αβ-4β,7β-methano-2H-inden-2-one, H, followed the main product closely. This isomer also forms under acidic equilibration.

EXAMPLE 5

(±)octahydro-1α-methyl-4aα,8aα,-5α,8α-methano-3H-2-benzopyran-3-one, I. To a solution of 3.81 g (23.2 mmole) of E in 50 mL of dry methylene chloride was added 5.5 g (4.67 g, 27 mmole) of 85% m-chloroperoxybenzoic acid. After three days the solids were removed by filtration and rinsed with hexane. The filtrate was washed with sodium bicarbonate, water and brine. After evaporation of solvents chromatography (Flash, hexane-EtOAc 98:2) provided 47 mg E with aryl-containing byproduct. This was followed by 4.02 g (96%) of I. Crystallization from a small amount of hexane provides solid melting at 51°-52.5°.

EXAMPLE 6

(±)octahydro-1α-methyl-4aα,8aα,-5α,8α-methano-1H-2-benzopyran-3-ol, J. A solution of 4.02 g (22.3 mmole) of I in 5 mL of toluene was chilled in a −78° bath and 30 mL of 1 M DIBAL in toluene was added and stirred at −78° for 2 h. The mixture was quenched cautiously with 5 mL of MeOH. After warming to room temperature, 50 mL more MeOH was added. The solid was removed by filtration, rinsing thoroughly with MeOH. The filtrate was evaporated, and the residue was crystallized from hexane to provide 3.23 g of J, mp 93°-94°. Chromatography of the mother liquors (Flash, 20-50% EtOAc-hexane) provided a small amount of crude I followed by a product fraction which was crystallized from hexane to provide an additional 0.33 g of J. Total yield: 3.56 g (88%).

EXAMPLE 7

(±)7-[3β-(1R*-hydroxyethyl)-1α,4α-bicyclo[2.2.1]hept-2β-yl-5Z-heptenoic acid, K. To a suspension of 13.5 g (30.6 mmole) freshly crushed and dried (60°, high vac) (4-carboxybutyl)triphenylphosphonium bromide in 75 mL dry THF was added 60 mL of a 1 M sodium (bistrimethylsilyl)amide in THF. The mixture was stirred at room temperature for 18 h under nitrogen and then a solution of 3.38 g (18.5 mmole) of J in 50 mL of THF was added over 10 min. The temperature rose from 27° to 35° during the addition. During 1 h the color faded quickly and more white solids formed. After the addition of 100 mL of water the mixture was extracted with ether. The aqueous layer was acidified with 10% HCl and extracted twice with ether washing with water and brine. After being dried over sodium sulfate the solvents were evaporated and the residue was chromatographed on a short acidic silica(such as Biosil A ® by Bio-Rad) column with 20% EtOAc-hexane to provide 4.90 g (99%) of a crude product fraction consisting of about 90% K and 10% of the 5E isomer, (±)7-3β-(1S-hydroxyethyl)-1α,4α-bicyclo[2.2.1]hept-2β-yl-5E-heptenoic acid, L. Traces of J could be recovered from the first ether extraction.

EXAMPLE 8

(±)7-(3β-acetyl-1α,4α-bicyclo[2.2.1]hept-2β-yl)-5Z-heptenoic acid, M and (±)7-(3α-acetyl-1α,4α-bicyclo[2.2.1]-hept-2β-yl)-5Z-heptenoic acid, O. A solution of 4.90 g (18.4 mmole) of crude K in 150 mL of acetone was chilled in an ice bath and titrated with Jones reagent (5.5 mL) until orange color persisted. The supernatant was decanted and concentrated to ca. 20 mL which was recombined with the solids and 100 mL of water. The mixture was extracted with ether. After washing with water and brine followed by drying over sodium sulfate the solvents were evaporated to leave 4.60 g of crude M with 10% of the 5E isomer (±)7-(3β-acetyl-1α, 4α-bicyclo[2.2.1]hept-2β-yl)-5E-heptenoic acid, N which had partially isomerized to O and its 5E isomer (±)7-(3α-acetyl -1α,4α-bicyclo[2.2.1]hept-2β-yl-5E-heptenoic acid, P. This material was dissolved in 50 mL of 1 N NaOH and stirred at room temperature for 1 h. After acidification with 10% HCl the product was extracted with ether which was washed with water and brine and dried over sodium sulfate. After evaporating solvents chromatography on a short acidic silica column (20% EtOAc-hexane) provided 4.38 g (90%) of a mixture containing ca. 90% O and 10% P. No trace of M or N could be detected.

EXAMPLE 9

(±)7-[3α-[[(phenylamino)thioxomethyl]hydrazonoethyl]-1α, 4α-bicyclo[2.2.1]hept-2β-yl]-5Z-heptenoic acid, SC-44161, and (±)7-[3α-[[(phenylamino)thioxomethyl]hydrazonoethyl]-1α, 4α-bicyclo[2.2.1]hept-2β-yl]-5E-heptenoic acid, SC-46986. A solution of 1.20 g (4.5 mmole) of the mixture of O and P in 5 mL of pyridine was stirred at room temperature for 22 h. A solution of the mixture in 100 mL of methylene chloride was washed twice with 100 mL 5% HCl, water and brine. After drying over sodium sulfate and evaporation of solvent the residue was crystallized from 10 mL of ether to provide 1.364 g (73%) of product, mp 129°-132°.

While the invention has been described and illustrated with reference to certain prepared embodiments and certain illustrative steps, those skilled in the art will appreciate that various changes, modifications and substitutions can be made therein without departing from the spirit and scope of the invention. It is intended therefore that the invention be limited only by the scope of the claims which follow, and that such claims be interpreted as broadly as is reasonable.

We claim:
1. A compound of the formula

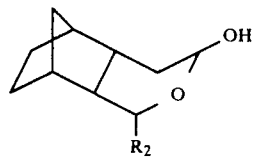

and the pharmaceutically acceptable salts thereof, wherein $R_2$ is selected from the group consisting of hydrogen, $C_{1-10}$ aliphatic hydrocarbon groups, and $C_{1-10}$ aliphatic hydrocarbon groups substituted by Ar, OAr or SAr, where Ar represents a phenyl, napthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups.

2. A compound as claimed in claim 1, in which $R_2$ is $C_{1-10}$ aliphatic hydrocarbon.

3. A Compound as claimed in claim 2, in which $R_2$ is methyl, namely ($\pm$)octahydro-1$\alpha$-methyl-4a$\alpha$, 8a$\alpha$,-5$\alpha$,8$\alpha$-methano-1H-2-benzopyran-3-ol,

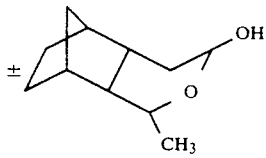

* * * * *